United States Patent
Raeder-Devens et al.

(10) Patent No.: US 9,545,299 B2
(45) Date of Patent: Jan. 17, 2017

(54) PROSTHESIS DEPLOYMENT DEVICE WITH TRANSLUCENT DISTAL END

(71) Applicant: Boston Scientific Scimed, Inc., Maple Grove, MN (US)

(72) Inventors: Jennifer E. Raeder-Devens, St. Paul, MN (US); Susan I. Shelso, Plymouth, MN (US); James F. Hemerick, Brooklyn Park, MN (US); Eric Schneider, Lincoln, RI (US); Heather Getty, Plymouth, MN (US); Doreen Borgmann, Hopkins, MN (US); Kakao Sisombath, Chanhassen, MN (US); Jeffrey A. Helgerson, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 51 days.

(21) Appl. No.: 14/027,792

(22) Filed: Sep. 16, 2013

(65) Prior Publication Data
US 2014/0013572 A1  Jan. 16, 2014

Related U.S. Application Data

(63) Continuation of application No. 13/554,533, filed on Jul. 20, 2012, now Pat. No. 8,535,369, which is a
(Continued)

(51) Int. Cl.
*A41B 13/04* (2006.01)
*B32B 3/00* (2006.01)
(Continued)

(52) U.S. Cl.
CPC . *A61F 2/02* (2013.01); *A61F 2/95* (2013.01); *A61F 2/966* (2013.01); *B29C 66/1122* (2013.01);
(Continued)

(58) Field of Classification Search
CPC .......... B29C 65/00; B29C 65/48; B29C 66/00; B29C 66/1122; B29C 66/5221; B29C 66/71; B29C 66/712; A61F 2/95; A61F 2/966; A61F 2/02; A61F 2/962; B32B 1/08; B32B 27/00; B32B 27/06; B32B 27/08; B32B 27/322; B32B 37/00; B32B 37/12
(Continued)

(56) References Cited

U.S. PATENT DOCUMENTS 2,857,915 A  4/1956  Sheridan
3,745,831 A  7/1973  Rothstein et al.
(Continued)

FOREIGN PATENT DOCUMENTS

CA  2204930 A1 *  11/1997  ............ A61M 25/01
EP  0812579  12/1997
(Continued)

*Primary Examiner* — Philip Tucker
*Assistant Examiner* — Brian R Slawski
(74) *Attorney, Agent, or Firm* — Seager, Tufte & Wickhem, LLP

(57) ABSTRACT

A prosthesis delivery and deployment device includes an elongate and flexible outer catheter. The outer catheter has a tubular wall of layered construction, including translucent layers, opaque layers, and a braid composed of helically wound metal filaments. The outer catheter has a translucent distal adapted to constrain a radially self-expanding prosthesis in a radially reduced, axially elongated state. Because the stent constraining region is translucent, an endoscope can be used to visually monitor the stent when so constrained. Radiopaque markers can be mounted to the outer catheter and to an inner catheter used to deploy the prosthesis, to afford a combined visual and fluoroscopic monitoring for enhanced accuracy in positioning the prosthesis, both before and during its deployment.

18 Claims, 2 Drawing Sheets

Related U.S. Application Data continuation of application No. 12/467,491, filed on May 18, 2009, now Pat. No. 8,226,702, which is a continuation of application No. 10/281,017, filed on Oct. 25, 2002, now abandoned, which is a continuation of application No. 09/569,445, filed on May 12, 2000, now Pat. No. 6,726,712.

(60) Provisional application No. 60/134,267, filed on May 14, 1999.

(51) Int. Cl.
| | | |
|---|---|---|
| *B65B 11/00* | (2006.01) | |
| *B29C 65/00* | (2006.01) | |
| *B32B 37/00* | (2006.01) | |
| *A61F 2/06* | (2013.01) | |
| *A61F 11/00* | (2006.01) | |
| *A61M 29/00* | (2006.01) | |
| *A61F 2/02* | (2006.01) | |
| *A61F 2/95* | (2013.01) | |
| *A61F 2/966* | (2013.01) | |
| *B32B 27/32* | (2006.01) | |
| *B32B 27/08* | (2006.01) | |

(52) U.S. Cl.
CPC .......... *B29C 66/5221* (2013.01); *B29C 66/712* (2013.01); *B32B 27/08* (2013.01); *B32B 27/322* (2013.01); *Y10T 29/49826* (2015.01)

(58) Field of Classification Search
USPC .............. 156/60, 64, 70, 148, 149, 157, 158, 242,156/244.11, 244.13, 296, 303.1, 304.1, 304.2,156/304.3, 293, 294, 278; 623/1.1, 1.11, 1.12, 623/1.23, 903; 606/108, 194, 198
See application file for complete search history.

(56) References Cited

U.S. PATENT DOCUMENTS

| | | | |
|---|---|---|---|
| 4,155,124 A | 5/1979 | Kawahara et al. | |
| 4,327,722 A | 5/1982 | Groshong et al. | |
| 4,365,050 A | 12/1982 | Ivani | |
| 4,411,276 A | 10/1983 | Dickhudt et al. | |
| 4,447,562 A | 5/1984 | Ivani | |
| 4,580,568 A | 4/1986 | Gianturco | |
| 4,655,771 A | 4/1987 | Wallsten | |
| 4,665,905 A | 5/1987 | Brown | |
| 4,668,861 A | 5/1987 | White | |
| 4,732,152 A | 3/1988 | Wallsten et al. | |
| 4,773,665 A | 9/1988 | Hindle | |
| 4,925,445 A | 5/1990 | Sakamoto et al. | |
| 4,954,126 A | 9/1990 | Wallsten | |
| 4,979,955 A | 12/1990 | Smith | |
| 5,024,232 A | 6/1991 | Smid et al. | |
| 5,026,377 A | 6/1991 | Burton et al. | |
| 5,027,792 A | 7/1991 | Meyer | |
| 5,061,275 A | 10/1991 | Wallsten et al. | |
| 5,090,408 A | 2/1992 | Spofford et al. | |
| 5,221,270 A | 6/1993 | Parker | |
| 5,269,750 A | 12/1993 | Grulke et al. | |
| 5,297,546 A | 3/1994 | Spofford et al. | |
| 5,304,577 A | 4/1994 | Nagata et al. | |
| 5,339,831 A | 8/1994 | Thompson | |
| 5,405,369 A | 4/1995 | Selman et al. | |
| 5,411,016 A | 5/1995 | Kume et al. | |
| 5,439,445 A | 8/1995 | Kontos | |
| 5,445,624 A * | 8/1995 | Jimenez ............ A61M 25/0009 604/264 |
| 5,457,728 A | 10/1995 | Whiting et al. | |
| 5,475,052 A | 12/1995 | Rhee et al. | |
| 5,480,432 A | 1/1996 | Suding et al. | |
| 5,496,294 A | 3/1996 | Hergenrother et al. | |
| 5,514,669 A | 5/1996 | Selman | |
| 5,534,007 A | 7/1996 | St. Germain et al. | |
| 5,545,149 A | 8/1996 | Brin et al. | |
| 5,563,233 A | 10/1996 | Reich et al. | |
| 5,565,519 A | 10/1996 | Rhee et al. | |
| 5,579,765 A | 12/1996 | Cox et al. | |
| 5,586,201 A | 12/1996 | Whiting et al. | |
| 5,599,305 A * | 2/1997 | Hermann et al. ......... 604/95.04 |
| 5,603,991 A | 2/1997 | Kupiecki et al. | |
| 5,609,600 A | 3/1997 | Love et al. | |
| 5,630,813 A | 5/1997 | Kieturakis | |
| 5,632,775 A | 5/1997 | Suding et al. | |
| 5,634,913 A | 6/1997 | Stinger | |
| 5,637,772 A | 6/1997 | Malik et al. | |
| 5,653,722 A | 8/1997 | Kieturakis | |
| 5,653,726 A | 8/1997 | Kieturakis | |
| 5,662,703 A | 9/1997 | Yurek et al. | |
| 5,679,299 A | 10/1997 | Gilbert et al. | |
| 5,679,470 A | 10/1997 | Mayer | |
| 5,702,418 A | 12/1997 | Ravenscroft | |
| 5,704,914 A | 1/1998 | Stocking et al. | |
| 5,718,159 A | 2/1998 | Thompson | |
| 5,725,519 A | 3/1998 | Penner et al. | |
| 5,728,762 A | 3/1998 | Reich et al. | |
| 5,733,248 A | 3/1998 | Adams et al. | |
| 5,766,192 A | 6/1998 | Zacca | |
| 5,769,830 A * | 6/1998 | Parker ............... A61M 25/0045 138/124 |
| 5,782,811 A | 7/1998 | Samson et al. | |
| 5,800,456 A | 9/1998 | Maeda et al. | |
| 5,800,511 A | 9/1998 | Mayer | |
| 5,800,541 A | 9/1998 | Rhee et al. | |
| 5,810,871 A | 9/1998 | Tuckey et al. | |
| 5,822,391 A | 10/1998 | Whiting et al. | |
| 5,824,041 A | 10/1998 | Lenker et al. | |
| 5,836,926 A * | 11/1998 | Peterson ........... A61M 25/0012 604/264 |
| 5,851,210 A | 12/1998 | Torossian | |
| 5,876,448 A | 3/1999 | Thompson et al. | |
| 5,879,400 A | 3/1999 | Merrill et al. | |
| 5,882,290 A | 3/1999 | Kume | |
| 5,897,584 A | 4/1999 | Herman | |
| 5,925,012 A | 7/1999 | Murphy-Chutorian et al. | |
| 5,925,445 A | 7/1999 | Suzuki | |
| 5,932,200 A | 8/1999 | Reich et al. | |
| 5,954,652 A | 9/1999 | Heyman | |
| 5,968,052 A * | 10/1999 | Sullivan et al. ............. 623/1.11 |
| 5,980,485 A | 11/1999 | Grantz et al. | |
| 5,989,245 A | 11/1999 | Prescott | |
| 6,019,778 A * | 2/2000 | Wilson et al. ................ 606/198 |
| 6,023,638 A | 2/2000 | Swanson | |
| 6,033,413 A | 3/2000 | Mikus et al. | |
| 6,093,194 A | 7/2000 | Mikus et al. | |
| 6,245,098 B1 | 6/2001 | Feeser et al. | |
| 6,514,261 B1 | 2/2003 | Randall et al. | |
| 6,726,712 B1 | 4/2004 | Raeder-Devens et al. | |
| 2001/0034549 A1 | 10/2001 | Bartholf et al. | |

FOREIGN PATENT DOCUMENTS

| | | |
|---|---|---|
| WO | 9740879 | 11/1997 |
| WO | 9823241 | 6/1998 |
| WO | 2005107646 | 11/2005 |

* cited by examiner

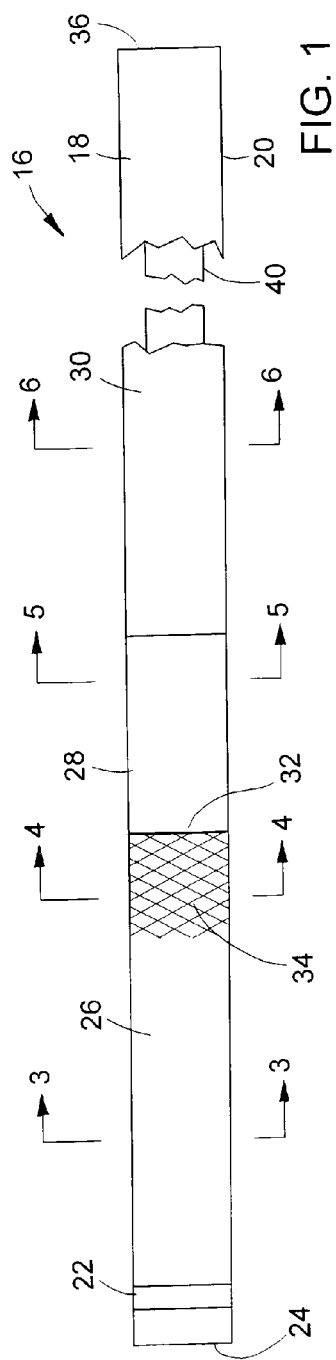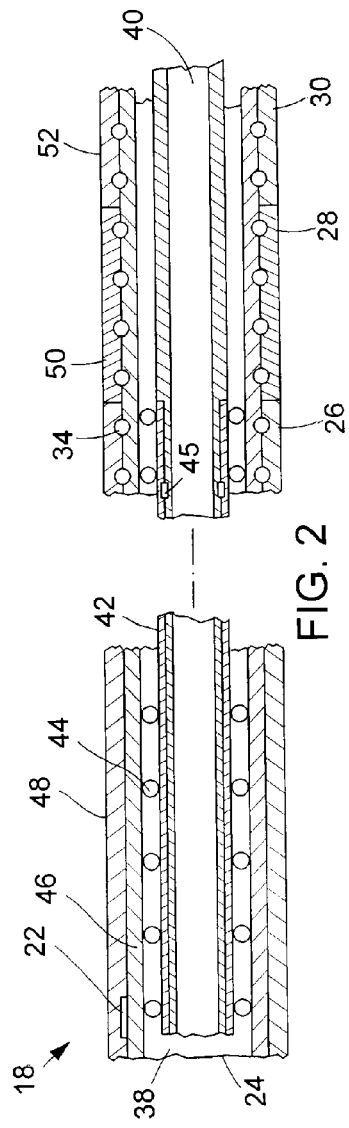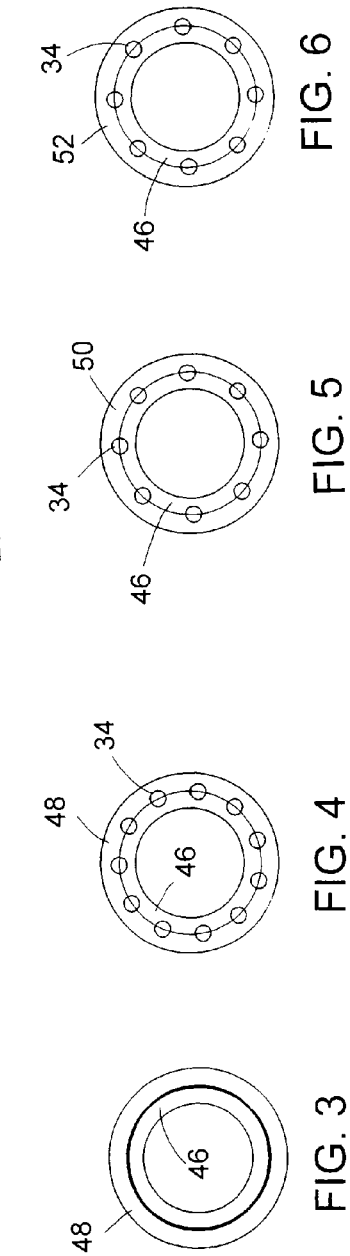

PROSTHESIS DEPLOYMENT DEVICE WITH TRANSLUCENT DISTAL END

CROSS-REFERENCE TO RELATED APPLICATIONS

This application is a continuation of U.S. application Ser. No. 13/554,533 filed Jul. 20, 2012, now U.S. Pat. No. 8,535,369, which is a continuation of U.S. application Ser. No. 12/467491 filed May 18, 2009, now U.S. Pat. No. 8,226,702, which is a continuation of U.S. application Ser. No. 10/281,017, filed Oct. 25, 2002, which is a continuation of U.S. application Ser. No. 09/569,445, filed May 12, 2000, now U.S. Pat. No. 6,726,712, which claims the benefit of priority of Provisional Application No. 60/134,267, filed May 14, 1999, the contents of each are incorporated herein by reference.

STATEMENT REGARDING FEDERALLY SPONSORED RESEARCH

Not Applicable

BACKGROUND OF THE INVENTION

The present invention relates to medical devices for delivering endoprostheses to predetermined treatment sites within body cavities or lumens, and further deploying the endoprostheses at the selected sites. More particularly, this invention relates to such devices that are capable of enabling or facilitating a tracking of the endoprostheses during deployment.

A variety of patient treatment and diagnostic procedures involve the use of prostheses inserted into the body of a patient and intraluminally implanted. Percutaneous translumenal coronary angioplasty (PTCA) and other vascular treatments frequently involve implanting prostheses such as stents to maintain vessel patency or grafts to shunt blood. Similar implantations are used in non-vascular procedures, e.g., enteral, billiary, and esophageal applications.

There is a need to accurately characterize the intended implant site to facilitate proper placement of the prosthesis. There is a further need, just before deployment and during deployment, to ascertain the location of the prosthesis relative to the intended placement site. One known approach to such characterizing and monitoring is angiography, which involves supplying a radiopaque contrast fluid to the cavity or lumen, then radiographically viewing the lumen. This approach, however, provides only a monochromatic, two-dimensional image showing a profile but no depth of field.

According to another approach, radiopaque markers can be placed on the delivery/deployment device. Before deployment, the position of the prosthesis within the device is known, and determining the device position in effect accurately determines the prosthesis position. This advantage is lost during deployment, however, and again the image offers neither distinctions in color nor depth of field.

According to yet another approach, the prosthesis can be fabricated at least in part using a radiopaque material. For example, the filaments of a stent can be formed of, or may incorporate a core formed of, platinum, tantalum or another radiopaque material. This approach likewise lacks the capacity for distinction among colors, and imposes limitations upon the materials used to form the prosthesis.

U.S. Pat. No. 5,411,016 discloses an intravascular balloon catheter having a lumen containing an angioscope. A distal portion of the catheter shaft, surrounded by the dilatation balloon, is transparent, and index markers are provided along the balloon. Thus, objects against which the balloon wall is pressed when the balloon is inflated can be quantified. This structure requires viewing the lumen through the catheter wall and the balloon wall, and does not address the need for monitoring the position of a prosthesis with respect to its delivery device during deployment. This need is particularly apparent in connection with radially self-expanding prostheses, which are constrained in radially reduced configurations during delivery, and must be released from their confining devices during deployment to permit radial self-expansion.

Therefore, it is an object of the present invention to provide a prosthesis delivery and deployment device that substantially surrounds a prosthesis to retain the prosthesis during delivery to a treatment site, yet facilitates an optical viewing of the prosthesis before and during its deployment. Another object is to provide a prosthesis delivery device particularly well suited to negotiate tortuous intraluminal pathways in the body that incorporates a translucent carrier segment through which a prosthesis carried within the device can be optically viewed.

A further object is to provide a process for deploying a radially self-expanding prosthesis within a body lumen in which an optical viewing device is advantageously used to view at least a proximal portion of the prosthesis to visually monitor a location of the prosthesis during its deployment.

Yet another object is to provide a catheter or other device for intraluminal delivery of a prosthesis, that incorporates a prosthesis confining wall sufficiently light transmissive to enable a viewing of the prosthesis through the wall, so that an optical instrument positioned within a body lumen outside the catheter can be used to observe the prosthesis contained in the delivery device, as well as tissue surrounding the delivery device.

BRIEF SUMMARY OF THE INVENTION

To achieve these and other objects, there is provided a prosthesis delivery and viewing device. The device includes an elongate, flexible catheter having a tubular catheter wall defining a catheter lumen. The catheter, along a distal end region thereof, is adapted to substantially surround a body insertable prosthesis and thereby releasably retain the prosthesis within the catheter lumen. The catheter wall, at least along the distal end region, is translucent to allow an optical viewing of the body insertable prosthesis through the catheter wall when the prosthesis is so retained.

Most preferably, the distal end region of the wall is substantially transparent, i.e., highly transmissive of wavelengths in the visible spectrum. Satisfactory viewing is achieved, if the distal end region wall merely is translucent; more particularly, sufficiently light transmissive so that at least about 25% of light impinging directly upon one side of the catheter wall is transmitted through the wall to the other side. A polyether block amide, for example as sold under the brand name Pebax, has been found to be well suited as a catheter wall material, not only due to its relative transparency, but also because it provides a ductile or flexible catheter wall that bonds well with other polymeric material. Certain nylons also can be used, although they are not as ductile as the Pebax material.

The device is advantageously used as part of a system that also includes an optical viewing device positionable proximate the distal end of the catheter to facilitate an optical viewing of the prosthesis and surrounding body lumen or cavity. An endoscope is suitable as such a viewing device.

According to one particularly preferred construction, the catheter includes an elongate, flexible translucent inner tubular body. A flexible, translucent first outer tube surrounds and is integral with a distal end region of the inner tubular body. An elongate, flexible second outer tube surrounds the inner tubular body, is integral with the inner tubular body, and is disposed proximally of the first outer tube. If desired, a flexible third outer tube is disposed between the first and second outer tubes, and contacts the other outer tubes to provide a substantially continuous profile composed of the three outer tubes. This construction allows a tailoring of the catheter, to provide a balance between two somewhat conflicting needs: sufficient flexibility to negotiate serpentine pathways; and sufficient columnar strength along the catheter length to provide the necessary axial pushing force.

In particular, such tailoring can involve selecting materials of different durometer hardness for the outer tubes. One highly preferred example uses a 63 Shore D durometer Pebax material in the first outer tube, and a 72 Shore D durometer Pebax material in the second, proximal outer tube which comprises most of the catheter length. To provide further columnar strength and resistance to kinking, a support structure can be interposed between the inner tubular layer and at least the second outer tube. A preferred structure is a braid of helically wound metal filaments, e.g., stainless steel or a cobalt-based alloy such as that sold under the brand name Elgiloy. If desired, the wire braid can extend distally beyond the second outer tube, and thus reside between the inner tubular layer and a proximal portion of the first outer tube, up to about one-half of the first outer tube length. When a third, medial outer tube is employed, it is preferably composed of a material having a 63 Shore D durometer hardness.

The delivery device further can include a prosthesis release component mounted moveably with respect to the catheter to effect a release of the prosthesis from within the catheter lumen. For example, an elongate flexible member, which can be a tube if desired, is disposed inside the catheter lumen and either abuts the proximal end of the prosthesis, or is surrounded by the prosthesis along its distal portion. In many cases the latter arrangement is more desirable, because it enables a retraction of the prosthesis after it is partially deployed, if repositioning is deemed necessary.

The delivery device is particularly well suited for use in a process for deploying a radially self-expanding prosthesis within a body lumen, including:
a. disposing a radially self-expanding prosthesis in a radially compressed state within a catheter, surrounded by a tubular wall of the catheter along a distal end region of the catheter;
b. moving the catheter intraluminally to position the distal end region of the catheter near a selected prosthesis deployment site within a body lumen;
c. with the catheter distal end region so positioned, initiating a release of the prosthesis from the catheter, and during the release, using an optical viewing device to optically view at least a proximal portion of the prosthesis through the catheter wall, to visually monitor a location of the prosthesis; and
d. after completing the release of the prosthesis, proximally withdrawing the catheter to leave the prosthesis disposed within the body lumen.

Thus in accordance with the present invention, a prosthesis can be optically viewed both before its release to insure an accurate positioning within a body lumen, and during its release to monitor its position both with respect to the lumen, and with respect to the delivery/deployment catheter. An endoscope or other suitable optical device can provide an image that enables the user to distinguish among colors, which can be beneficial in recognizing properties of the tissue at the treatment site. Optical images also afford depth of field. The capability of optically viewing the lumen and prosthesis when still contained within the catheter, combined with fluoroscopic imaging of the catheter and the prosthesis, provides particularly effective monitoring of the deployment and positioning of the prosthesis.

BRIEF DESCRIPTION OF THE DRAWINGS

For a further understanding of the above and other features and advantages, reference is made to the following detailed description and to the drawings, in which:

FIG. 1 is a side elevation of a prosthesis delivery and deployment device constructed in accordance with the present invention;

FIG. 2 is an enlarged elevation, partially sectioned to show further features of the device;

FIGS. 3, 4, 5 and 6 are sectional views taken respectively along the lines 3-3, 4-4, 5-5, and 6-6 in FIG. 1;

DETAILED DESCRIPTION OF THE INVENTION

Figure 7:
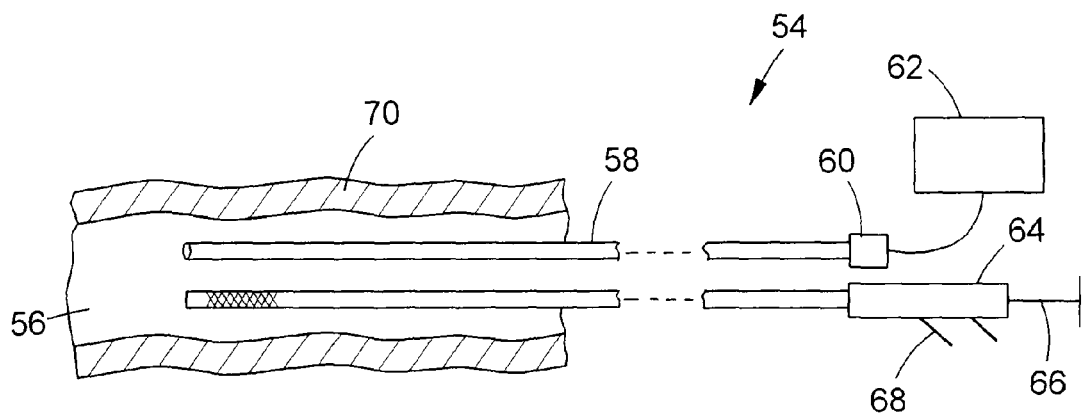
FIG. 7 is a schematic view of a prosthesis deployment and viewing system incorporating the deployment device.

Turning now to the drawings, there is shown a device 16 for delivering a radially self-expanding prosthesis to a selected treatment site within a body cavity or body lumen, and for deploying the prosthesis, once it is positioned at the treatment site. The device includes an elongate, flexible outer catheter 18 having a tubular catheter wall 20. A radiopaque marker 22 is mounted to the catheter near its distal end 24.

Along its axial length, catheter wall 20 is divided into three sections or regions: a distal region 26; a medial region or transition region 28; and a proximal region 30. As indicated by the break, the full length of proximal region 30 is not shown in FIG. 1. The proximal region is by far the longest of the three regions. The diameter and axial length of catheter 18 can vary according to the application and size of the body lumen involved. Some typical ranges for enteral applications include a total catheter length of 135-230 cm in conjunction with a distal segment length of 7-18.5 cm, a transition region length of 6-7.5 cm, and a diameter of 5-22 French, i.e. about 1.7-3.0 mm.

Distal region 26 extends from distal end 24 to a junction 32 between two slightly different polymeric materials employed in forming the catheter wall. Along the distal region, the catheter wall preferably is transparent, exhibiting a high transmissivity of energy in the visible spectrum. Less preferably but satisfactorily, catheter wall 20 is translucent along the distal region, in the sense that at least 25% of the energy in the visible spectrum impinging directly upon catheter 18 is transmitted through catheter wall 20 to the other side. A braid 34 formed of helically wound intersecting filaments of stainless steel, a cobalt-based alloy or other suitable metal, forms a layer of catheter wall 20 beginning at a distal region that is visible due to the transparency of the polymeric layer surrounding it. The braid extends proximally to a proximal end 36 of the catheter, provides a reinforcing structure that increases the columnar strength of medial region 28 and proximal region 30, and also increases radial stability and resistance to kinking when catheter 18 is bent.

FIG. 2 shows device 16, particularly the distal and medial sections, in greater detail. Outer catheter 18 includes a catheter lumen 38 that runs substantially the entire catheter length. An inner catheter 40, contained in lumen 38, is movable axially relative to outer catheter 18. Inner catheter 40 extends lengthwise substantially along the entire length of the outer catheter. A sleeve 42 surrounds inner catheter 40 along a distal portion of the catheter comparable to catheter distal region 26 in its axial length. A prosthesis, in particular a radially self-expanding stent 44, surrounds the inner catheter and sleeve along the distal portion of the inner catheter. Stent 44 in turn is surrounded by the distal region of outer catheter 18, constrained by the outer catheter wall in a radially reduced, axially elongated state. Stent 44 is radially self-expanding, in that once free of the outer catheter, the stent tends to shorten axially and expand radially to a normal or unstressed shape in which the stent diameter is much larger than the diameter of the outer catheter. Stent 44 is somewhat similar to braid 34, in that the stent is composed of oppositely directed helically wound filaments or wires that intersect one another. However, because the filaments forming stent 44 typically are smaller in diameter than the filaments forming braid 34, the filaments of the stent frequently are formed of materials selected for enhanced radiopacity, e.g. a composite construction including a tantalum core within an Elgiloy casing. A radiopaque marker 45 is located along inner catheter 40, between the inner catheter and the sleeve.

The layered, segmented construction of catheter wall 20 is best seen in FIG. 2. Catheter wall 20 includes an inner layer, i.e. a PTFE liner 46 that extends for the length of the catheter. Liner 46 is substantially translucent to transparent, typically with an amber cast. Liner 46 typically is etched to improve bonding adhesion to the layers that surround it.

The surrounding layers, or outer tubes, include a transparent or translucent outer distal layer 48, an opaque outer medial layer 50, and an opaque outer proximal layer 52. Marker 22 is disposed between liner 46 and distal outer layer 48. Beginning near the proximal end of outer layer 48 and extending proximally for the remainder of the catheter length, braid 34 is interposed between outer layer 48, medial outer layer 50 and proximal outer layer 52. The outer layers are bonded to the liner. Consequently, the liner, outer layers, marker and braid are integral with one another.

In accordance with the present invention, materials are selected for the liner and outer layers to impart desired properties that differ over the length of catheter 18. As noted above, liner 46 is formed of PTFE. The inside surface of liner 46 preferably is coated with silicone, to provide a low-friction surface to contact stent 44 and facilitate axial travel of inner catheter 40 relative to the outer catheter. Liner 46 is cylindrical, and can have for example an inner diameter of 0.117 inches and a radial thickness of 0.0015 inches.

Over the majority of the catheter length, the next radially outward layer is composed of braid 34. The filaments of braid 34 can be stainless steel wires, having a diameter of about 0.015 inches. In one advantageous arrangement, 32 wires are wound helically, interbraided in a two-over-two-under pattern, at about 52 pics per inch. The braid angle can be 110-150 degrees, i.e. 55-75 degree inclines from a longitudinal axis.

At the distal end of catheter 18, radiopaque marker 22 is provided in the form of an annular band surrounding liner 46. The band can be formed of a platinum/iridium alloy, and can have a diameter of 0.127 inches and radial thickness of about 0.0015 inches.

Distal outer layer 48 surrounds and is bonded to liner 46. The preferred material for the distal outer layer is a polyether block amide available under the brand name "Pebax," with a 63 ShoreD durometer hardness. Outer layer 48 is substantially transparent. Accordingly, liner 46 and outer layer 48 in combination provide a catheter wall region that is substantially transparent, or at least sufficiently translucent so that stent 44, when contained within catheter 18 as shown in FIG. 2, is visible from outside the catheter through the catheter wall. Another favorable property of outer layer 48 is its relatively high flexibility, whereby the distal region is well suited for initial tracking through serpentine body passages as the catheter is moved toward an intended treatment site. Distal outer layer 48 can have a diameter of about 1.17 inches, and a thickness of about 0.010 inches.

Medial outer layer 50 also is preferably constructed of the Pebax polyether block amide, having the same 63 Shore D durometer hardness. The polymer is combined with a blue dye, and thus forms an opaque layer. Outer layer 50 can have an axial length of about 5 cm, an inner diameter of about 0.129 inches, and a radial thickness of about 0.012 inches. Due to the contrast between the translucent outer layer 48 and the opaque outer layer 50, junction 32 provides a clear visible marker that locates the proximal end of stent 44 when the stent is radially constrained by the outer catheter.

Transition region 28 includes the full length of outer layer 50, and in addition the length of braid 34 extending distally into distal region 26. Although the visible distal extension of the braid can include half the length of distal region 26 and even more if desired, this extension typically is in the range of 1-2.5 cm. The transition region thus combines braid 34 and the 63 D durometer hardness Pebax polymer, with part of the polymer being translucent and part being opaque. Transition region 28 is flexible, although less flexible than the distal region. The braid reduces kink potential. Proximal outer layer 52 is formed of a Pebax polymer having a 72 Shore D durometer hardness. The proximal outer layer can have an inner diameter of 0.129 inches and a radial thickness of 0.012 inches, same as the medial outer layer. Also like the medial layer, proximal outer layer 52 is combined with a blue dye to render this region of the catheter opaque. The higher durometer hardness of the proximal outer layer provides enhanced column strength, thus to provide the axial pushing force necessary for advancing the catheter distally through body passages.

Less highly preferred but satisfactory results may be achieved when forming the various catheter wall components using alternative materials. For example, several grades of nylon including nylon 12 may be used to form outer layers 48, 50 and 52. A suitable alternative material for liner 46 is polyurethane, e.g. as available under the brand name Pellethane. A nylon available under the brand name Amitel is suitable for the outer layers, although better suited for the opaque outer layers than translucent outer layer 48.

Inner catheter 40 is preferably formed of polyether ether ketone (PEEK). The polymer forming sleeve 42 preferably is substantially softer and more flexible than the other polymers, so that stent 44 when disposed between the catheters as shown in FIG. 2 tends to embed itself into the sleeve.

FIG. 7 illustrates a system 54, including device 16, for delivering and deploying stent 44 within a body lumen 56.

The system includes an endoscope 58 positionable within body lumen 56 proximate distal region 26 of the catheter. Although the endoscope is represented schematically, it is to be understood that the endoscope can incorporate a light source 60, an optical fiber or other suitable optical path to transmit light to the distal end of the endoscope, an optical fiber, bundle of fibers or other suitable path to transmit images proximally along the endoscope, and a display terminal 62 for displaying the visible image. The proximal end of outer catheter 18 is coupled to a manifold 64. A handle 66, coupled to inner catheter 40 and movable relative to the manifold, controls axial movement of the inner catheter relative to the outer catheter. Additional fittings 68 are provided for a variety of purposes depending on the procedure, potentially including accommodating a guidewire, transmitting a therapeutic drug to the distal end of the catheter, and accommodating a balloon inflation fluid for a dilatation balloon.

System 54 is used in a stent implant procedure as follows. First, a guidewire or guide canula is used to track endoscope 58 to the selected implant site. Likewise, a guidewire (not shown) is tracked to the site.

Next, device 16 is loaded onto the guidewire and tracked to the site. The flexibility of the distal section improves cornering through the body passages on the way to the site. Meanwhile, proximal region 30 provides the column strength necessary to push the device toward the site. Braid 34 provides resistance to kinking, combined with the ability to track tight radii.

As distal end 24 of the device approaches the treatment site, junction 32 between translucent and opaque regions provides a reliable visible indication to locate the proximal end of the constrained stent 44.

Once the catheter distal end is positioned as desired, stent 44 is deployed, by pulling outer catheter 18 proximally while controlling handle 66 to maintain inner catheter 40 in place. Due to the softness of sleeve 42 and the lubricity of silicone coated liner 46, stent 44 tends to remain with the inner catheter rather than moving proximally with the outer catheter.

As the outer catheter continues to move proximally, distal end 24 is carried proximally with respect to the distal end of the stent, thus partially freeing the stent for radial self-expansion. Because of the translucency of the outer catheter wall along distal end region 26, endoscope 58 can be used continuously during deployment to monitor the position of stent 44, relative to body lumen 56 and relative to inner catheter 40. Moreover, as outer catheter 18 continues to move axially relative to inner catheter 40, radiopaque marker 22 likewise moves axially relative to marker 45, thus to permit a fluoroscopic monitoring of the outer catheter axial position relative to the inner catheter. Markers 22 and 45 can be positioned such that as marker 22 approaches marker 45, a limit approaches beyond which deployment cannot be reversed, i.e. when the stent no longer can be drawn back into outer catheter 18 by advancing the outer catheter distally relative to the inner catheter. The combined visual and fluoroscopic monitoring enables the user to more precisely confirm an appropriate positioning of the stent before exceeding the limit.

Beyond the limit, outer catheter 18 is moved proximately until stent 44 is completely free of the outer catheter. This leaves the stent free to radially self-expand to its nominal diameter. The nominal diameter typically exceeds a diameter of body lumen 56, so that the stent self-expands into an intimate contact with a tissue wall 70 defining the body lumen. With the implant of the stent thus complete, endoscope 58 and device 16 are proximally withdrawn, leaving the stent implanted at the treatment site.

Figure 8:
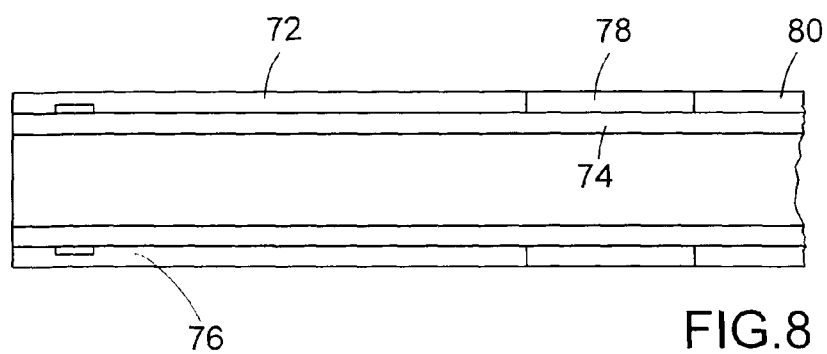
FIG. 8 is a side elevation illustrating an alternative embodiment deployment device.

FIG. 8 illustrates a portion of an alternative embodiment outer catheter 72 including a single liner 74 and several outer layers including a distal outer layer 76, medial outer layer 78 and proximal outer layer 80 as before. Outer catheter 72 differs from outer catheter 18, in that all three of the outer layers are translucent or substantially transparent, providing an outer catheter that is translucent or substantially transparent over its entire length.

Figure 9:
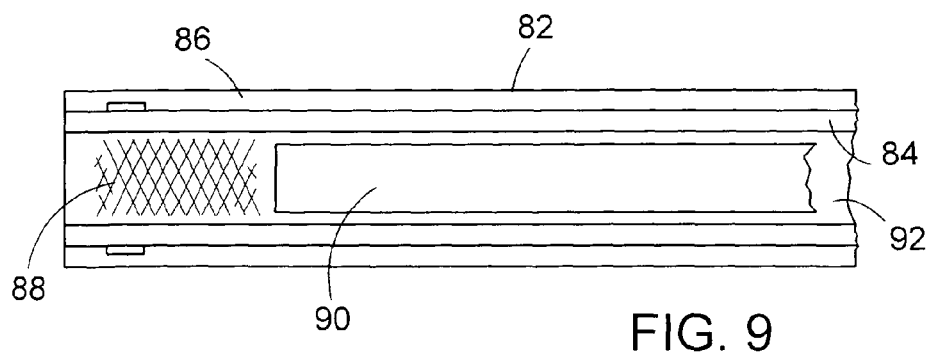
FIG. 9 is a side elevation illustrating another alternative embodiment deployment device.

FIG. 9 illustrates an outer catheter 82 of another alternative embodiment device, including an inner liner 84 and a single outer layer 86 running substantially the entire outer catheter length. A body implantable stent 88 is constrained along the distal region of the outer catheter, in a radially reduced axially elongated state. An inner catheter 90 is contained within a lumen 92 of the outer catheter. Rather than being surrounded by the stent, inner catheter 90 is disposed proximally of the stent, and movable distally relative to the outer catheter to engage the proximal end of the stent. Catheter 90 deploys the stent by pushing the stent distally relative to catheter 82. While this approach is suitable for certain procedures, and may reduce the cost of the device, it also lacks the capability of reversing stent deployment to reposition the stent.

Thus, in accordance with the present invention, a prosthesis can be visually monitored during its deployment, even when substantially or entirely contained within the deployment catheter. When provided with layers of differing flexibility over the catheter length, the catheter can be sufficiently flexible at its distal end for efficient tracking, yet sufficiently rigid along its more proximal regions to insure adequate distal pushing force. Further, radiopaque markers can be employed to enable fluoroscopic monitoring of device components as well as visual monitoring of the device and stent, to insure that the stent not only is properly aligned at the outset of deployment, but remains in the desired position as it is released from the deployment device.

The invention claimed is:

1. A method of forming a catheter with a longitudinal length, the method comprising:
    bonding a distal outer tube, the distal outer tube being either translucent or transparent, to a distal region of an inner tube having a longitudinal length equal to the longitudinal length of the catheter, the inner tube also comprising a proximal region, and a medial region extending between and connecting the distal and proximal regions,
    wherein the distal region of the inner tube is either translucent or transparent;
    bonding a medial outer tube to the medial region of the inner tube, the medial outer tube being opaque;
    bonding a proximal outer tube to the inner tube, the proximal outer tube being opaque; and
    interposing a support structure between the inner tube and the proximal, medial, and distal outer tubes and bonding the support structure thereto, wherein the support structure extends from a proximal end of the inner tube to a position that is proximal to a distal end of the inner tube and distal to a distal end of the medial outer tube, the support structure positioned such that a stent disposed in the distal region of the catheter extends distal of the support structure.

2. The method of claim 1, wherein the inner tube comprises PTFE and the distal, medial, and proximal outer tubes comprise polyether block amide.

3. The method of claim 2, wherein the medial and proximal outer tubes further comprise a dye.

4. The method of claim 2, wherein the polyether block amide of the distal and medial outer tubes has a lower Shore D durometer than the polyether block amide of the proximal outer tube.

5. The method of claim 4, wherein the Shore D durometer of the distal and medial outer tubes is 63±15 and the Shore D durometer of the proximal outer tube is 72±15.

6. The method of claim 1, wherein the support structure comprises metal filaments.

7. The method of claim 6, wherein the metal filaments are in the form of a braid.

8. The method of claim 1, further comprising coating an inner surface of the inner tube with silicone.

9. The method of claim 1, further comprising coupling a manifold to a proximal end of the catheter.

10. A method for forming a prosthesis delivery system comprising:
    positioning an inner catheter having a handle at a proximal end, the inner catheter comprising a wall defining a lumen and comprising a first inner catheter polymer, in a lumen defined by a wall of an outer catheter comprising:
        an inner tube having a longitudinal length equal to the longitudinal length of the outer catheter, the inner tube comprising a distal region, a proximal region, and a medial region extending between and connecting the distal and proximal regions, the distal region of the inner tube being either translucent or transparent;
        a distal outer tube bonded to the distal region of the inner tube, the distal outer tube being either translucent or transparent;
        a medial outer tube bonded to the medial region of the inner tube, the medial outer tube being opaque; and
        a proximal outer tube bonded to the proximal region of the inner tube, the proximal outer tube being opaque;
    interposing a support structure between the inner tube and the proximal, medial, and distal outer tubes and bonding the support structure thereto;
    wherein the inner catheter is movable axially relative to the outer catheter; and
    disposing a radially self-expanding prosthesis in a compressed state on a prosthesis deployment region, wherein the prosthesis deployment region is defined by a distal region of the inner catheter and by a distal region of the outer catheter, the distal region of the outer catheter formed by the distal region of the inner tube and the distal outer tube;
    wherein the support structure extends from a proximal end of the inner tube to a position that is proximal to a distal end of the inner tube and distal to a distal end of the medial outer tube, the support structure positioned such that the radially self-expanding prosthesis disposed in the distal region of the outer catheter extends distal of the support structure.

11. The method of claim 10, wherein the inner tube comprises PTFE and the distal, medial, and proximal outer tubes comprise polyether block amide.

12. The method of claim 11, wherein the medial and proximal outer tubes further comprise a dye.

13. The method of claim 11, wherein the polyether block amide of the distal and medial outer tubes has a lower Shore D durometer than the polyether block amide of the proximal outer tube.

14. The method of claim 13, wherein the Shore D durometer of the distal and medial outer tubes is 63±15 and the Shore D durometer of the proximal outer tube is 72±15.

15. The method of claim 10, wherein the support structure comprises metal filaments.

16. The method of claim 15, wherein the metal filaments are in the form of a braid.

17. The method of claim 10, further comprising coating an inner surface of the inner tube with silicone.

18. A method for forming a prosthesis delivery system comprising:
    providing an outer catheter with a manifold at a proximal end, the outer catheter comprising a multi-layer wall defining a lumen, the multi-layer wall comprising:
        an inner tube with a distal region, a proximal region, and a medial region extending between and connecting the distal and proximal regions;
        a distal outer tube bonded to the distal region of the inner tube, wherein the distal outer tube and the distal region of the inner tube are either translucent or transparent;
        a medial outer tube bonded to the distal outer tube and the medial region of the inner tube;
        a proximal outer tube bonded to the medial outer tube and the proximal region of the inner tube, wherein the proximal outer tube is opaque; and
        a support structure interposed between the inner tube and a proximal portion of the distal outer tube;
    providing an inner catheter with a handle at a proximal end, the inner catheter comprising a wall defining a lumen, the wall comprising a first inner catheter polymer;
    positioning the inner catheter in the lumen of the outer catheter, the inner catheter movable axially relative to the outer catheter; and
    disposing a radially self-expanding prosthesis in a compressed state on a prosthesis deployment region, wherein the prosthesis deployment region is defined by a distal region of the inner catheter and by a distal region of the outer catheter, the distal region of the outer catheter formed by the distal region of the inner tube and the distal outer tube;
    wherein the radially self-expanding prosthesis disposed on the prosthesis deployment region extends distal of the support structure.

* * * * *